United States Patent
Gall et al.

(10) Patent No.: US 9,443,315 B2
(45) Date of Patent: Sep. 13, 2016

(54) METHOD AND SYSTEM TO PROCESS MAGNETIC RESONANCE DIFFUSION IMAGE DATA

(71) Applicant: Siemens Aktiengesellschaft, Munich (DE)

(72) Inventors: Peter Gall, Buckenhof (DE); Heiko Meyer, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/554,308

(22) Filed: Nov. 26, 2014

(65) Prior Publication Data

US 2015/0146956 A1 May 28, 2015

(30) Foreign Application Priority Data

Nov. 27, 2013 (DE) ........................ 10 2013 224 264

(51) Int. Cl.
| | | |
|---|---|---|
| G06K 9/00 | (2006.01) | |
| G06T 7/00 | (2006.01) | |
| G01R 33/563 | (2006.01) | |
| A61B 5/055 | (2006.01) | |

(52) U.S. Cl.
CPC ....... *G06T 7/0081* (2013.01); *G01R 33/56341* (2013.01); *A61B 5/055* (2013.01); *G06T 2207/10088* (2013.01); *G06T 2207/20148* (2013.01); *G06T 2207/30004* (2013.01)

(58) Field of Classification Search
USPC .................................................. 382/128–134
See application file for complete search history.

(56) References Cited

U.S. PATENT DOCUMENTS

| | | | | |
|---|---|---|---|---|
| 5,268,967 A | * | 12/1993 | Jang ....................... | G06T 7/0012 382/132 |
| 5,694,490 A | * | 12/1997 | Howell .................. | G06T 7/0012 382/128 |
| 2003/0223628 A1 | * | 12/2003 | Meyer ..................... | G06T 15/08 382/128 |
| 2004/0106864 A1 | * | 6/2004 | Rose ....................... | A61B 5/055 600/410 |
| 2007/0249931 A1 | * | 10/2007 | Fain .................. | G01R 33/56341 600/420 |
| 2008/0007264 A1 | | 1/2008 | Ichinose | |
| 2008/0069417 A1 | | 3/2008 | Kimura | |
| 2008/0319302 A1 | * | 12/2008 | Meyer .................. | A61B 5/0263 600/410 |
| 2009/0034812 A1 | * | 2/2009 | Nowinski ............... | A61B 5/055 382/131 |
| 2009/0096448 A1 | * | 4/2009 | Meredith ......... | G01R 33/56341 324/309 |
| 2009/0129649 A1 | * | 5/2009 | Djeridane ............. | G06T 7/0014 382/131 |

(Continued)

FOREIGN PATENT DOCUMENTS

WO 2010/116124 A1 10/2010

OTHER PUBLICATIONS

"Differential MRI diagnosis between brain abscesses and necrotic or cystic brain tumors using the apparent diffusion coefficient and normalized diffusion-weighted images," Desbarats et al., Magnetic Resonance Imaging, vol. 21 (2003), pp. 645-650.

(Continued)

*Primary Examiner* — Alex Liew
(74) *Attorney, Agent, or Firm* — Schiff Hardin LLP (57) ABSTRACT

In a method, a user interface, a magnetic resonance apparatus, and a storage medium encoded with programming instructions, in order to enable processing and/or display of magnetic resonance diffusion image data, diffusion image data are provided to a computer, a signal threshold are provided to a computer, and a b-value map is calculated by the computer on the basis of the diffusion image data and the predetermined signal threshold.

8 Claims, 3 Drawing Sheets

(56) References Cited

U.S. PATENT DOCUMENTS

2009/0208083 A1* 8/2009 Hayes .................. G01R 33/543
   382/131
2013/0259340 A1* 10/2013 Tseng ............... G01R 33/56341
   382/131

OTHER PUBLICATIONS

"Comparison of Apparent Diffusion Coefficients and Distributed Diffusion Coefficients in High-Grade Gliomas," Kwee et al., Journal of Magnetic Resonance Imaging, vol. 31 (2010), pp. 531-537.

* cited by examiner

METHOD AND SYSTEM TO PROCESS MAGNETIC RESONANCE DIFFUSION IMAGE DATA

BACKGROUND OF THE INVENTION

1. Field of the Invention

The invention concerns a method to process magnetic resonance diffusion image data, as well as a user interface, a magnetic resonance apparatus, and a non-transitory, computer-readable data storage medium encoded with programming instructions for implementing such a method.

2. Description of the Prior Art

In magnetic resonance diffusion imaging, multiple diffusion images with different diffusion directions and/or diffusion weightings, which are typically characterized by a b-value, are normally acquired. A diffusion coefficient map can then be created from the diffusion images, for example. This is a spatially resolved depiction of apparent diffusion coefficients (ADC). The apparent diffusion coefficient typically describes the average length of a trajectory of a water molecule in tissue. If the length of the trajectory is long, the water molecules can move freely and the apparent diffusion coefficient is large. If the movement of the water molecules is prevented, such as due to a high cell density in compact tissue, which may be due to a tissue variation, the apparent diffusion coefficient is small. The diffusion images and/or the diffusion coefficient map are designated as diffusion image data.

SUMMARY OF THE INVENTION

An object of the invention is to enable a particularly advantageous processing and/or display of magnetic resonance diffusion image data.

A method in accordance with the invention for processing diffusion image data of an examination subject acquired by a magnetic resonance apparatus, includes the following steps: provide diffusion image data to a computer, provide a signal threshold to the computer, and in the computer, calculate a b-value map on the basis of the diffusion image data and the predetermined signal threshold.

The provision of the diffusion image data to the computer can be acquisition of the diffusion image data by a magnetic resonance apparatus. Alternatively or additionally, the provision of the diffusion image data can be a loading of previously acquired diffusion image data into the computer, for example from a database.

The provided diffusion image data typically includes at least two diffusion images, the at least two diffusion images having different diffusion weightings, in particular different b-values. The diffusion weighting is typically dependent on the formation of diffusion gradients that are used during the acquisition of the diffusion images. As noted, the strength of the diffusion weighting is typically described by a b-value, with a higher b-value indicating a stronger diffusion weighting, for example due to a higher amplitude and/or a longer duration of the diffusion gradients. The diffusion images typically include a spatial distribution of magnetic resonance signals acquired with a diffusion weighting, known as diffusion signals. A diffusion image may have no or only a weak diffusion weighting, thus a b-value of nearly zero. The diffusion images can be three-dimensional and then, for example, can include multiple two-dimensional slice images that together form a three-dimensional diffusion image.

The diffusion image data may already include at least one diffusion coefficient map. A diffusion coefficient map typically includes a spatial distribution of diffusion coefficients (namely apparent diffusion coefficients) of the examination subject that are measured by the magnetic resonance apparatus. A calculation of a diffusion coefficient map typically takes place on the basis of the at least two diffusion images. Alternatively, an already-calculated diffusion coefficient map may be loaded directly in the provision of the diffusion image data, such as from a database.

The method according to the invention is based on the insight that diffusion images with special (in particular high) b-values are often relevant to an assessment by an expert personnel. In these diffusion images, for example, compact tissue with a low apparent diffusion coefficient is especially emphasized. However, the b-value used in the acquisition of the diffusion images has a direct influence on the echo time of an acquisition sequence. Higher b-values typically lead to longer echo times. Given the use of higher b-values, the signal-to-noise ratio of the diffusion images therefore typically decreases. Therefore, typically at least two diffusion images with small or medium b-values are used to determine the diffusion coefficient map. However, the b-values of the at least two diffusion images should also be markedly different so that the precision of the determination of the apparent diffusion coefficient is improved. It is typically not known in advance which b-values are necessary for assessment of the diffusion images, for example for clear delimitation of compact or injured tissue, nor it is known in advance for which b-value such tissue can best be differentiated from normal tissue. In order to enable a best possible differentiation, many diffusion images with different b-values must often be acquired, so the measurement time for acquisition of the diffusion images is very high, and it may still occur that a diffusion image with a special b-value that would be of interest has not been acquired. Therefore, in conventional methods for processing diffusion image data, diffusion images are typically extrapolated that have different virtual b-values from the measured b-values. Since the optimal b-value is unknown before the calculation, many diffusion images with virtual b-values must often be calculated, of which only a small part is relevant to expert personnel for the assessment of the diffusion images. This generates unnecessary data in a database and a high workload for expert personnel, who must seek out relevant diffusion images from the large number of diffusion images with the different virtual b-values.

The calculation of the b-value map on the basis of the diffusion image data and the predetermined signal threshold in accordance with the invention is advantageous compared to conventional methods for processing of diffusion image data. The b-value map produced in accordance with the invention advantageously includes a spatial distribution of those b-values for which a diffusion signal measured by the magnetic resonance apparatus has the predetermined signal threshold. Magnetic resonance signals, in particular diffusion signals, typically decrease with increasing b-values. That b-value for which the spatially resolved diffusion signal reaches the predetermined signal threshold and/or falls below the predetermined signal threshold can then be stored in a parameter map (the b-value map). The b-value map advantageously needs to be calculated only once from the predetermined signal threshold and the diffusion image data, in particular of the diffusion coefficient map calculated from the diffusion image data. The calculation of the b-value map thus saves computing time and evaluation time. The b-value map simultaneously offers the versatility of many diffusion images with different diffusion weightings. In particular, the b-value map includes virtual b-values and can thus also be designated as a virtual b-value map. The b-value map is in fact calculated on the basis of diffusion image data that have been acquired with defined b-values. The b-value map is advantageously not limited to these defined b-values, however, but rather includes a broader spectrum of (in particular virtual) b-values and/or additional (in particular virtual) b-values. The b-value map is thus not limited to one b-value. The b-value map thus saves on additional tools to assess diffusion image data. The b-value map also reduces the workload of an expert personnel since he or she only needs to assess one image (the b-value map) instead of possibly many diffusion images. After the calculation of the b-value map, the b-value map can be made available electronically as a data file, for example by display at a display unit, storage in a database, and/or transfer to an additional computer, etc.

In an embodiment, a display of the calculated b-value map takes place. The b-value map can be displayed at a display unit (for example a monitor), in particular in a user interface. The displayed b-value map can then be viewed and/or assessed by a user, in particular an expert personnel. Expert personnel can set parameters for the displayed b-value map via an input unit. For example, the user can modify the slice of the b-value map that is to be displayed and/or the contrast of the b-value map, for example by means of adjusting the signal threshold.

In another embodiment, the display of the calculated b-value map includes a windowing of the calculated b-value map. This allows the user to produce the windowing of the b-value map. For this purpose, the user can select a windowing of the displayed b-value map, for example in order to display specific tissue (in particular compact tissue) with a low apparent diffusion coefficient (and thus a high b-value) with a desired contrast in the b-value map. In particular, low b-values in the b-value map can be masked out to show the compact tissue with a high b-value. This means that the windowing is advantageously set such that tissue with low b-values is shown black in the b-value map, such that compact tissue with a high b-value particularly clearly emerges. For example, the windowing can include the setting of a minimum b-value and a window width for the b-value. All b-values that are smaller than the minimum b-value are then shown as black in the b-value map, for example. All b-values which are greater than the window width added to the minimum b-value are then shown as white in the b-value map. B-values lying in-between are shown in greyscale depending on their formation, for example. Naturally, another method for windowing of the b-value map (for example the adjustment of a window width and a middle point of the window) is also possible. Naturally, a color presentation of the b-value map according to a color palette can also be chosen. A windowing of the displayed b-value map is particularly advantageous because observers (in particular expert personnel) of medical image data (diffusion image data, for example) are accustomed to a windowing of the image data and implement this intuitively. A windowing of the b-value map also advantageously requires no recalculation of the b-value map, and accordingly saves on computing resources. Nevertheless, through the windowing the b-value map can have a particularly advantageous and significant contrast.

In another embodiment, the provision of the signal threshold includes a determination of the signal threshold using the diffusion image data and/or additional magnetic resonance image data. The signal threshold can be calculated using an algorithm. It can therefore be calculated so that the b-value map is displayed with an advantageous contrast, and thus has a clear significance to an observing expert personnel. The automatic calculation of the signal threshold can also represent an advantageous starting point for a later change of the signal threshold which in particular includes a recalculation of the b-value map due to an input by the user in an input unit.

In another embodiment the predetermination of the signal threshold includes an input to the computer by a user via an input unit. The user can thus provide an advantageous signal threshold for calculation of the b-value map. The entry of the signal threshold can be based on a b-value map that is already displayed, in particular with an automatically determined signal threshold. With the input of the signal threshold, the user can modify the b-value map such that the b-value map is displayed to the user at a desired contrast so that an advantageous and particularly simple assessment of the b-value map is possible.

A user interface according to the invention has an image data acquisition unit, a specification unit and a computer, wherein the image data acquisition unit, the specification unit and the computer are designed to execute a method for processing diffusion image data of an examination subject acquired by means of at least one magnetic resonance apparatus, wherein the image data acquisition unit is designed to receive diffusion image data, the specification unit is designed to provide a signal threshold, and the computer is designed for calculation of a b-value map on the basis of the diffusion image data and the predetermined signal threshold.

The image data acquisition unit can be designed for loading the diffusion image data, in particular from a database. The image data acquisition unit can also be designed to receive the diffusion image data from a magnetic resonance apparatus.

Embodiments of the user interface according to the invention are designed analogous to the embodiments of the method according to the invention. According to an embodiment, the user interface thus has a display unit that is designed to display the calculated b-value map. According to another embodiment, the display unit is designed so that, dependent on an entry made by a user via an input unit of the user interface, the display of the calculated b-value includes a windowing of the calculated b-value map. According to another embodiment, the specification unit (in particular a computing module of the specification unit) is designed to implement a determination of the signal threshold using the diffusion image data and/or additional magnetic resonance image data. This step can also be implemented by the computer of the user interface, which includes the specification unit. According to one embodiment, the specification unit comprises an input unit, wherein the provision of the signal threshold includes an input of the signal threshold into the input unit by a user.

The user interface can have additional control components that are necessary and/or advantageous for execution of a method according to the invention. The user interface can also be designed to send control signals to a magnetic resonance apparatus and/or to receive and/or process control signals in order to execute a method according to the invention. Computer programs and additional software can be stored in a memory unit of the user interface, by means of which computer programs and additional software a processor of the user interface automatically controls and/or executes a method workflow of a method according to the invention. The user interface according to the invention thus enables a processing and/or display of diffusion image data that especially saves computing time, is versatile and is significant.

The magnetic resonance apparatus according to the invention has an image data acquisition unit, a specification unit and a computer, wherein the image data acquisition unit, the specification unit and the computer are designed to execute a method to process diffusion image data of an examination subject that are acquired by a data acquisition unit, in which a patient is situated, of the magnetic resonance apparatus, wherein the image data acquisition unit is designed to require diffusion image data, the specification unit is designed to provide a signal threshold, and the computer is designed to calculate a b-value map on the basis of the diffusion image data and the predetermined signal threshold.

In particular, the image data acquisition unit is designed to receive diffusion image data for the data acquisition unit. The image data acquisition unit can also be designed to load the diffusion image data, in particular from a database. Embodiments of the magnetic resonance apparatus according to the invention are designed analogous to the embodiments of the method or of the user interface according to the invention. For this purpose, computer programs and additional software can be stored in a memory unit of the magnetic resonance apparatus, by means of which computer programs and additional software a processor of the magnetic resonance apparatus automatically controls and/or executes a method workflow of a method according to the invention. The magnetic resonance apparatus according to the invention thus enables a processing and/or display of diffusion image data that especially saves computing time, is versatile and is significant.

The present invention also encompasses a non-transitory, computer-readable data storage medium encoded with programming instructions that, when the storage medium is loaded into a computer or processor of a user interface or a magnetic resonance apparatus, cause the interface or the magnetic resonance apparatus to execute any or all embodiments of the method described above. The computer must thereby respectively have the requirements (for example a corresponding working memory, a corresponding graphics card or a corresponding logic unit) so that the respective method steps can be executed efficiently. The control information of the electronically readable data medium is designed to implement a method according to the invention given use of the data medium in a computer of a user interface and/or of a magnetic resonance apparatus. Examples of electronically readable data media are a DVD, a magnetic tape or a USB stick on which is stored electronically readable control information, in particular software (see above). All embodiments according to the invention of the method described in the preceding can be implemented when this control information (software) is read from the data medium and stored in a controller and/or computer of a user interface and/or of a magnetic resonance apparatus.

The advantages of the user interface according to the invention, of the magnetic resonance apparatus according to the invention and of the computer program product according to the invention essentially correspond to the advantages of the method according to the invention are described above. The corresponding functional features of the method are developed by corresponding objective modules, in particular by hardware modules.

DESCRIPTION OF THE PREFERRED EMBODIMENTS

Figure 1:
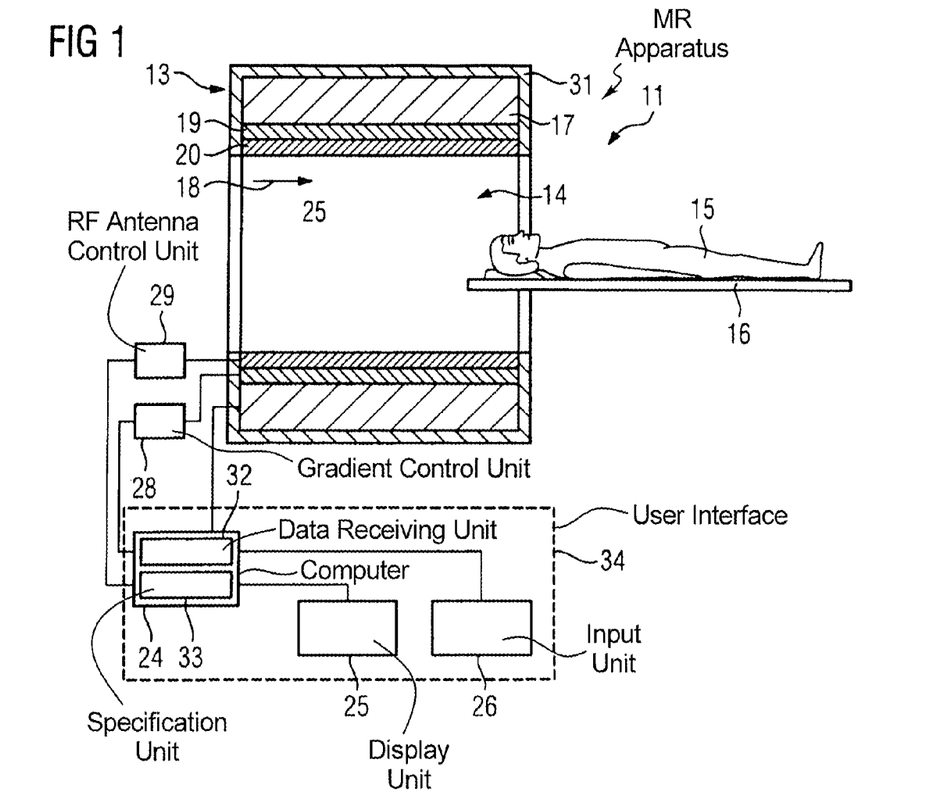
FIG. 1 schematically illustrates a magnetic resonance apparatus according to the invention for execution of the method according to the invention.

FIG. 1 shows a magnetic resonance (MR) apparatus 11 according to the invention for execution of the method according to the invention. The magnetic resonance apparatus 11 has a detector unit formed by a magnet unit 13, with a basic magnet 17 to generate a strong and in particular constant basic magnetic field 18. In addition to this, the magnetic resonance apparatus 11 has a cylindrical patient accommodation region 14 to accommodate an examined person 15 (in particular a patient 15), wherein the patient accommodation region 14 is cylindrically enclosed by the magnet unit 13 in a circumferential direction. The patient 15 can be slid into the patient accommodation region 14 by means of a patient bearing device 16 of the magnetic resonance apparatus 11. For this purpose, the patient bearing device 16 has a table bed that is arranged so as to be movable within the magnetic resonance apparatus 11. The magnet unit 13 is externally shielded by a housing 31 of the magnetic resonance apparatus 11.

The magnet unit 13 furthermore has a gradient coil unit 19 to generate magnetic field gradients that are used for a spatial coding during an imaging. The gradient coil unit 19 is controlled by means of a gradient control unit 28. Furthermore, the magnet unit 13 has: a radio-frequency (RF) antenna unit 20 which, in the shown case, is designed as a body coil permanently integrated into the magnetic resonance apparatus 11, and a radio-frequency antenna control unit 29 to excite a polarization that arises in the basic magnetic field 18 generated by the basic magnet 17. The radio-frequency antenna unit 20 is controlled by the radio-frequency antenna control unit 29 and radiates radio-frequency magnetic resonance sequences into an examination space that is essentially formed by the patient accommodation region 14. The radio-frequency antenna unit 20 is furthermore designed to receive magnetic resonance signals, in particular from the patient 15.

To control the basic magnet 17, the gradient control unit 28 and the radio-frequency antenna control unit 29, the magnetic resonance apparatus 11 has a computer 24. The computer 24 centrally controls the magnetic resonance apparatus 11, for example the implementation of a predetermined imaging gradient echoes. Control information (for example imaging parameters) as well as reconstructed magnetic resonance images can be displayed to an operator at a display unit 25—for example on at least one monitor—of the magnetic resonance apparatus 11. In addition to this, the magnetic resonance apparatus 11 has an input unit 26 by means of which information and/or parameters can be input by an operator during a measurement process and/or a display process of image data. The computer 24 can directly pass control commands to the gradient control unit 28 and the radio-frequency antenna control unit 29. Furthermore, the computer comprises an image data receiving (acceptance) unit 32 and a specification unit 33. The computer with the image data acquisition unit 32 and the specification unit 33, the display unit 25 and the input unit 26 form a user interface 34, which is likewise designed to execute a method according to the invention.

The shown magnetic resonance apparatus 11 can naturally include additional components that magnetic resonance apparatuses conventionally have. The general functioning of a magnetic resonance apparatus 11 is known to those skilled in the art, such that a more detailed description of the additional components is not necessary herein.

Figure 2:
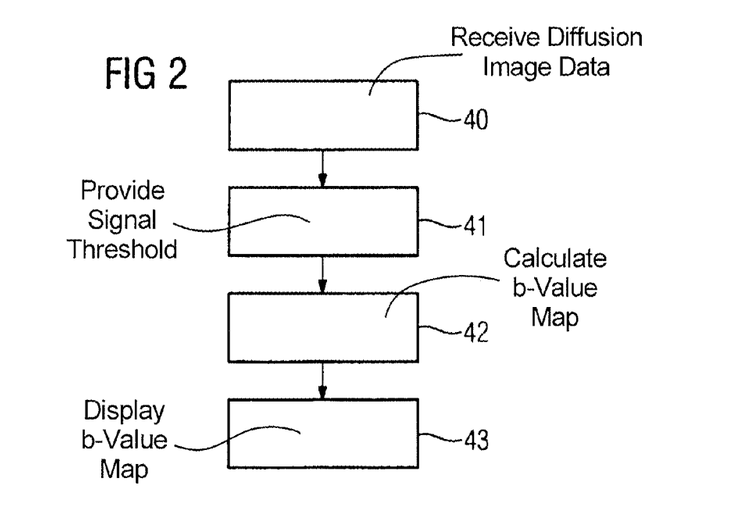
FIG. 2 is a flowchart of an embodiment of the method according to the invention.

FIG. 2 shows a flowchart of an embodiment of the method according to the invention for processing of diffusion image data of a patient 15 that are acquired by the magnetic resonance apparatus 11. In a first method step 40, an acquisition of diffusion image data takes place by means of the image data acquisition unit 32 and/or the magnetic resonance apparatus 11. In a further method step 41, a provision of a signal threshold takes place by means of the specification unit 33. In a further method step 42, a calculation of a b-value map takes place by means of the computer 24 on the basis of the diffusion image data and the provided signal threshold. In a further method step 43, a display of the calculated b-value map takes place by means of the display unit 25.

Figure 3:
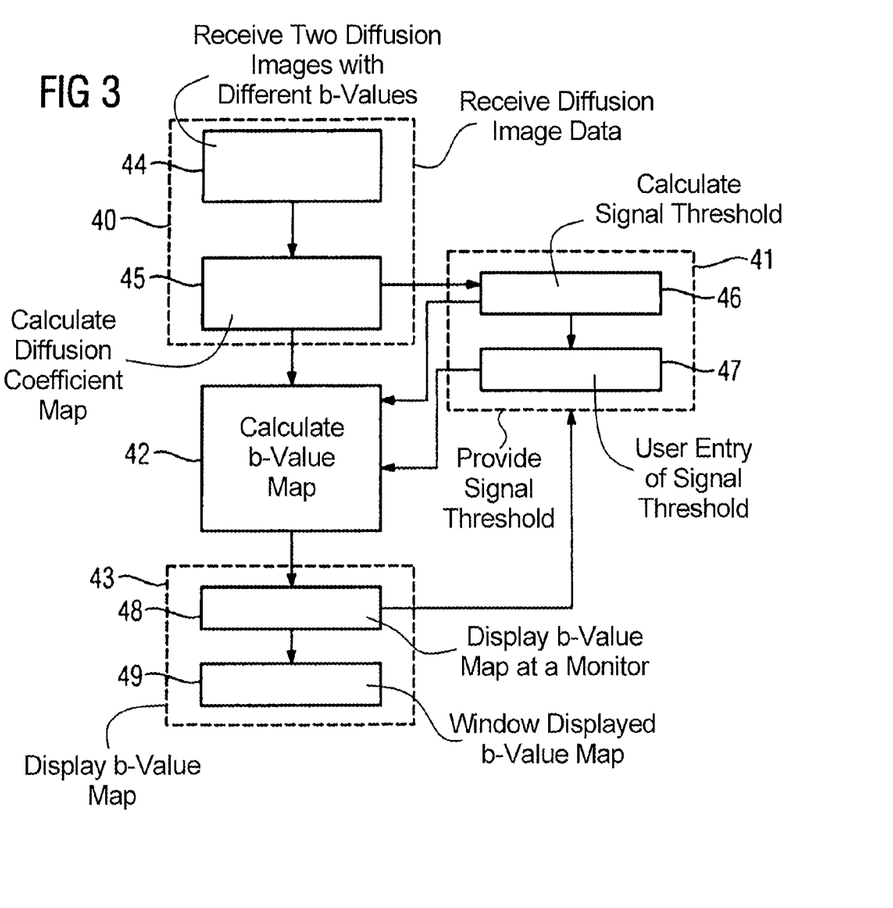
FIG. 3 is a more detailed flowchart of an embodiment of the method according to the invention.
Figure 5:
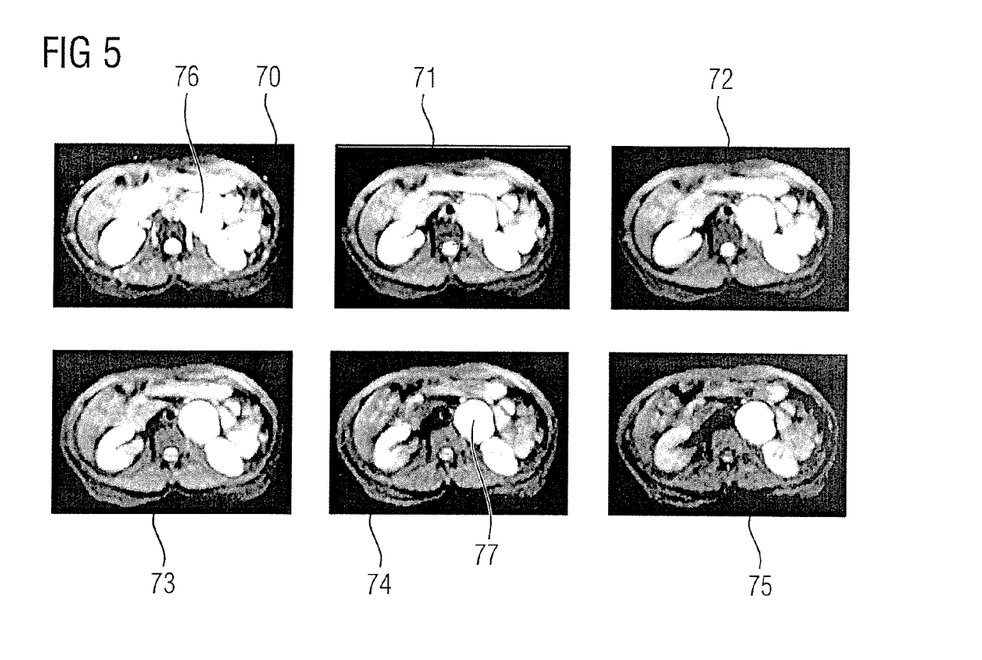
FIG. 5 depicts six diffusion images acquired from the same examination subject with the same field of view, but with different b-values.

FIG. 3 shows a more detailed workflow diagram of an embodiment of a method according to the invention. The four underlying method steps from FIG. 2 are here provided with sub-steps according to an advantageous embodiment. These sub-steps (described in the following) are hereby to be viewed only as optional and exemplary. The acquisition of the diffusion image data in the first method step 40 includes a first acquisition step 44 in which an acquisition of at least two diffusion images takes place by means of the magnetic resonance apparatus 11. The at least two diffusion images are thereby acquired with different b-values. One b-value of the two different b-values can thereby also amount to zero, such that the acquisition of a diffusion image takes place without diffusion weighting. In FIG. 5, six diffusion images 70, 71, 72, 73, 74, 75 of an examination subject that are acquired with different b-values are shown with the same field of view, which diffusion images 70, 71, 72, 73, 74, 75 are arranged ascending according to the value of the b-value. For example, the second diffusion image 71 was acquired with a higher b-value—and thus with a higher diffusion weighting—than the first diffusion image 70. The third diffusion image 72 was acquired with a higher b-value than the second diffusion image 71 etc. It can be seen that the signal strength in the diffusion images 70, 71, 72, 73, 74, 75 decreases with increasing b-values. At the same time, the signal-to-noise ratio also decreases with increasing b-values, whereby the image quality of the diffusion images 70, 71, 72, 73, 74, 75 decreases with increasing b-values. However, in diffusion images 70, 71, 72, 73, 74, 75 with higher b-values an exemplary tissue mass 76, 77 with compact tissue (for example a tumor or tissue affected by a stroke) is clearly emphasized. The tissue mass 77 in fifth diffusion image 74 is thus more clearly demarcated from its environment than the tissue mass 76 in the first diffusion image 70. An acquisition of diffusion images 70, 71, 72, 73, 74, 75 with higher b-values thus leads to an improved contrast between the tissue mass and surrounding tissue given a simultaneous loss of signal-to-noise ratio.

Furthermore, the acquisition of the diffusion image data in the first method step 40 includes a second acquisition step 45 in which a calculation of a diffusion coefficient map takes place by means of the computer 24 (in particular the image data acquisition unit 32) on the basis of the at least two acquired diffusion images. The calculation of the diffusion coefficient map from the at least two acquired diffusion images takes place by means of known methods. The diffusion coefficient map is required later for the calculation of the b-value map using said diffusion coefficient map. The diffusion coefficient map and/or the diffusion images hereby represent the diffusion image data which are acquired by the image data acquisition unit 32 in the first method step 40.

The provision of the signal threshold by means of the specification unit 33 in the further method step 41 includes a first specification step 46 in which a calculation of the signal threshold takes place by means of the computer 24 (in particular the specification unit 33) on the basis of the diffusion image data and/or additional image data. An advantageous signal threshold is determined automatically by execution of an algorithm on the basis of the diffusion images and/or diffusion coefficient map acquired in the first method step 40.

The additional method step 41 includes a second specification step 47, wherein an input of the signal threshold by a user into the input unit 26 takes place. The user can hereby adapt the signal threshold calculated in the first specification step 46. This can take place on the basis of a b-value map displayed at the display unit 25, with the b-value map being recalculated and displayed after adaptation of the signal threshold by the user.

In the further method step 42, the b-value map is calculated by means of the computer 24 on the basis of the diffusion image data acquired in the further method step 40 and on the basis of the signal threshold provided in the further method step 41.

The calculation of the b-value map from the diffusion coefficient map is illustrated in the following in a very simple, abstracted formula. The calculation for an image point and/or a voxel of the diffusion coefficient map and the corresponding image point and/or voxel of the b-value map is described. The simplest expression of the relationship between a diffusion signal S in a diffusion image which was acquired given a defined b-value b and an apparent diffusion coefficient ADC is:

$$S = S_0 * \exp(-b * \text{ADC})$$

wherein $S_0$ is the value of the diffusion signal that was measured with a b-value of zero or was extrapolated from a b-value of zero. Resolved for b, the relationship is:

$$b = -\frac{1}{\text{ADC}} * \ln\left(\frac{S}{S_0}\right)$$

If a signal threshold $S_{TH}$ for S is now provided, a b-value $b_{TH}$ can thus be calculated in which a diffusion signal measured by means of the magnetic resonance apparatus has the predetermined signal threshold:

$$b_{TH} = -\frac{1}{\text{ADC}} * \ln\left(\frac{S_{TH}}{S_0}\right)$$

The b-value map then advantageously includes the b-values $b_{TH}$ for each image point and/or a voxel of the diffusion coefficient map. The b-value map thus likewise includes a spatially resolved depiction of the b-values $b_{TH}$. It is noted again that the described shown method for calculation serves only for illustration, and that an actual method for calculation of the b-value map advantageously takes into account additional terms (for example an additional perfusion in tissue that is present for diffusion and/or other molecule types than water).

However, in the present formula it is already apparent that tissue types with different apparent diffusion coefficients ADC have different b-values in the b-value map. Compact tissue with a small apparent diffusion coefficient $ADC_T$ hereby has a large b-value $b_{TH}$. Tissue types—in particular normal tissue and/or water—with a large apparent diffusion coefficient ADC have a small b-value $b_{TH}$. This is clarified in the diagram of FIG. 4. Here the natural logarithm of a diffusion signal S measured in a diffusion image is plotted on a diffusion signal axis 60 over a b-value axis 61 with b-values b with which the diffusion image was acquired. The dependency of the diffusion signal S on the b-value b is shown for two different tissue types. A water curve 64 shows the dependency of the logarithm of the diffusion signal of aqueous tissue on the b-value. A tissue mass curve 66 shows the dependency of the logarithm of the diffusion signal of compact tissue (in particular a tissue mass) on the b-value. Given a b-value of zero—thus given diffusion images which were acquired without diffusion weighting—the water curve 64 and the tissue mass curve 66 have the same diffusion signal, and thus meet at an intersection point 63. The absolute value of the slope of the water curve 64 (which corresponds to the diffusion coefficient $ADC_W$ of aqueous tissue) is hereby greater than the absolute value of the slope of the tissue mass curve 66 (which corresponds to the diffusion coefficient $ADC_T$ of compact tissue). If a signal threshold 62 for the diffusion signal is now provided, the water curve 64 reaches the signal threshold 62 at a first b-value 65, wherein the tissue mass curve 66 reaches the signal threshold 62 at a second b-value 67. Due to the different diffusion coefficients $ADC_W$ of the aqueous tissue and $ADC_T$ of the compact tissue (and thus different slopes of the water curve 64 and the tissue mass curve), the first b-value 65 is smaller than the second b-value 67. The compact tissue thus can be clearly differentiated from aqueous tissue in the b-value map. Naturally, the shown curves 64, 66 are only exemplary, schematic and in particular idealized, since they ignore perfusion effects, for example.

After calculation of the b-value map, an additional processing of the b-value map can still take place—for example by filtering and/or masking of image noise—to increase the image quality of the b-value map.

The display of the calculated b-value map in the further method step 43 includes a first display step 48 in which the b-value map calculated in the additional method step 42 is displayed at a display unit 25 (in particular a monitor). The b-value map can be shown in a two-dimensional presentation in slice images. The possibility is then provided to the user to select the different slice images for display by means of the input unit 26. The b-value map can also advantageously be shown in a maximum intensity projection (MIP).

The display of the calculated b-value map in the further method step 43 includes a second display step 49 in which a windowing of the calculated b-value map takes place. The windowing can be implemented by a user by means of the input unit 26. The displayed b-value map is thereby shown windowed, whereby the contrast between compact tissue and aqueous tissue in the displayed b-value map can be improved, for example.

Figure 6:
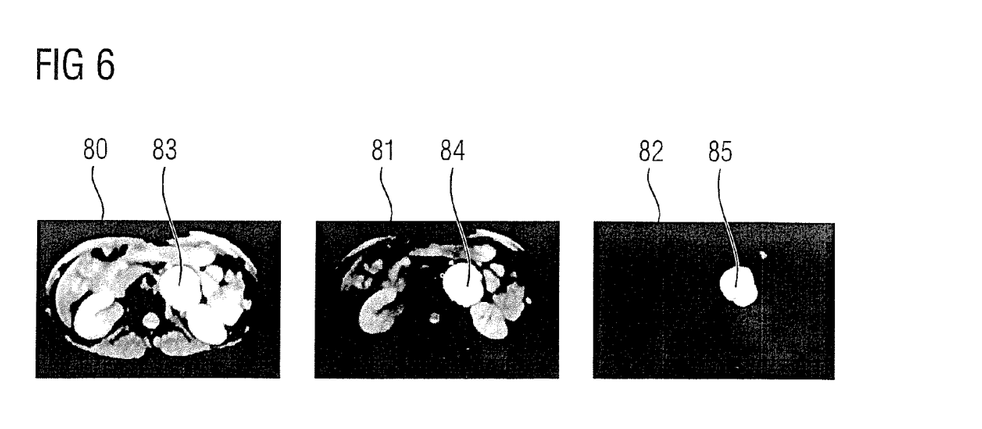
FIG. 6 shows three depictions of a b-value map with different windowings, with the same field of view as in FIG. 5.

Shown in FIG. 6 is a b-value map in a first windowing 80, a second windowing 81 and a third windowing 82. Each windowing 80, 81, 82 hereby shows the same tissue mass 83, 84, 85 in a respective different windowed presentation. The field of view and the examination subject of the b-value map of FIG. 6 correspond to the field of view and the examination subject of FIG. 5. FIG. 6 shows that a distinct contrast between compact tissue of the tissue mass 83, 84, 85 and surrounding tissue can be achieved exclusively by means of a windowing of the b-value map. While the tissue mass 83 of the first windowing 80 is just barely set apart from the surrounding tissue, the tissue mass 84 of the second windowing 81 can already be clearly differentiated from the surrounding tissue. The tissue mass 85 of the third windowing 82 is even more clearly prominent. In contrast to the presentation of the tissue mass 76, 77 in the diffusion images 70, 71, 72, 73, 74, 75 of FIG. 5, the improved contrast between compact tissue and surrounding tissue due to the windowing of the b-value map that is depicted in FIG. 6 leads to no losses in the signal-to-noise ratio. Furthermore, the b-value map includes only one image which must be assessed by expert personnel, in particular by windowing.

Figure 4:
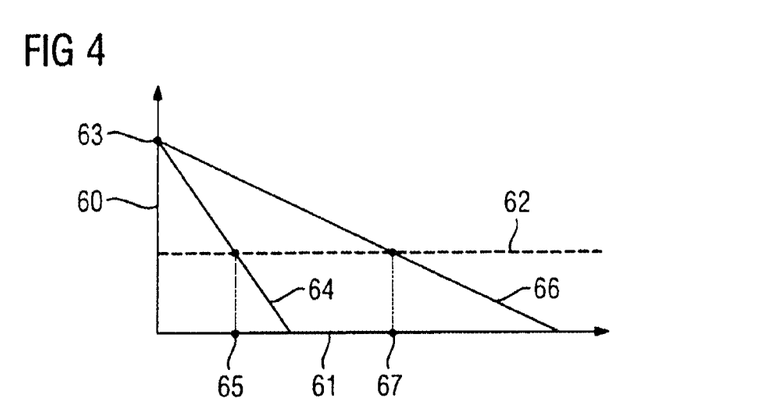
FIG. 4 schematically depicts the dependency of a diffusion signal of a diffusion image on a b-value that was used to acquire the diffusion image, for aqueous tissue and compact tissue.

The method steps of the method according to the invention that are presented in FIG. 2 and FIG. 3 and illustrated in FIG. 4 and FIG. 6 are executed by the magnetic resonance apparatus 11, in particular the user interface 34 of the magnetic resonance apparatus 11. For this, the computer 24 of the magnetic resonance apparatus 11—in particular the computer 24 of the user interface 34 of the magnetic resonance apparatus 11—includes necessary software and/or computer programs that are stored in a memory unit of the computer 24. The software and/or computer programs include program means that are designed to execute the method according to the invention when the computer program and/or the software is executed in the computer 24 by a processor of the magnetic resonance apparatus 11, in particular a processor of the user interface 34 of the magnetic resonance apparatus 11.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to process diffusion image data acquired by magnetic resonance from an examination subject, comprising:
    providing magnetic resonance diffusion image data to a computer;
    providing said computer with a designation of a signal threshold;
    in said computer, automatically calculating a b-value map from said diffusion image data and said predetermined signal threshold; and
    making said b-value map available in electronic form, as a data file, from an output of the computer.

2. A method as claimed in claim 1 comprising providing said data file to a display in communication with said computer, and displaying the calculated b-value map at said display.

3. A method as claimed in claim 2 comprising, at said display, windowing the displayed b-value map.

4. A method as claimed in claim 1 wherein providing said signal threshold to said computer comprises determining, in said computer, said signal threshold using at least said diffusion image data or additional magnetic resonance image data obtained from the subject.

5. A method as claimed in claim 1 comprising providing said signal threshold as a user input into said computer via an input unit.

6. A method as claimed in claim 1 comprising calculating said b-value map as a spatial distribution of respective b-values for which a diffusion signal in said magnetic resonance diffusion image data as a predetermined diffusion signal threshold.

7. A computerized user interface device to process diffusion image data acquired by magnetic resonance from an examination subject, comprising:
    a computer having an input configured to receive magnetic resonance diffusion image data;
    said computer comprising a specification unit configured to provide a signal threshold;
    in said computer being configured to automatically calculate a b-value map from said diffusion image data and said predetermined signal threshold;
    said computer being configured to make said b-value map available in electronic form, as a data file, from an output of the computer; and
    a display monitor in communication with said computer, said display monitor receiving said output from said computer and displaying said b-value map at a display screen of said display monitor.

8. A non-transitory, computer-readable data storage medium encoded with programming instructions, said data storage medium being loaded into a computer and said programming instructions causing said computer to:
    receive magnetic resonance diffusion image data;
    receive or generate a designation of a signal threshold;
    calculate a b-value map from said diffusion image data and said predetermined signal threshold; and
    make said b-value map available in electronic form, as a data file, from an output of the computer.

* * * * *